(12) United States Patent
Lee et al.

(10) Patent No.: US 10,130,725 B2
(45) Date of Patent: Nov. 20, 2018

(54) METHOD FOR LABELING EXOSOMES WITH RADIOACTIVE SUBSTANCE AND USE THEREOF

(71) Applicants: SNU R&DB FOUNDATION, Seoul (KR); POSTECH ACADEMY-INDUSTRY FOUNDATION, Gyeongsangbuk-do (KR)

(72) Inventors: Dong Soo Lee, Seoul (KR); Do Won Hwang, Seoul (KR); Hongyoon Choi, Seoul (KR); Yun-Sang Lee, Seoul (KR); Jae Min Jeong, Seoul (KR); Yong Song Gho, Gyeongsangbuk-do (KR); Su Chul Jang, Gyeongsangbuk-do (KR)

(73) Assignees: SNU R&DB FOUNDATION, Seoul (KR); POSTECH ACADEMY—INDUSTRY FOUNDATION, Gyeongsangbuk-Do (KR)

( * ) Notice: Subject to any disclaimer, the term of this patent is extended or adjusted under 35 U.S.C. 154(b) by 87 days.

(21) Appl. No.: 15/313,274

(22) PCT Filed: May 13, 2015

(86) PCT No.: PCT/KR2015/004778
§ 371 (c)(1),
(2) Date: Nov. 22, 2016

(87) PCT Pub. No.: WO2015/178618
PCT Pub. Date: Nov. 16, 2015

(65) Prior Publication Data
US 2017/0143856 A1 May 25, 2017

(30) Foreign Application Priority Data
May 22, 2014 (KR) .................. 10-2014-0061609

(51) Int. Cl.
*A61K 51/12* (2006.01)
*G01N 33/60* (2006.01)

(52) U.S. Cl.
CPC ...... *A61K 51/1217* (2013.01); *A61K 51/1203* (2013.01); *G01N 33/60* (2013.01)

(58) Field of Classification Search
CPC .............................. A61K 51/00; G01N 33/60
See application file for complete search history.

(56) References Cited

FOREIGN PATENT DOCUMENTS

| KR | 10-2010-0030195 A | 3/2010 |
|---|---|---|
| KR | 10-1106533 B1 | 1/2012 |
| KR | 10-1130737 B1 | 3/2012 |
| KR | 10-2013-0127276 A | 11/2013 |

OTHER PUBLICATIONS

Dongmei Sun et al. A Novel Nanoparticle Drug Delivery System: The Anti-inflammatory Activity of Curcumin is Enhanced when Encapsulated in Exosomes, Molecular Therapy, vol. 18(9), 1606-1614. (Year: 2010).*
International Search Report for PCT/KR2015/004778.
Su Chul Jang et al., Bioinspired Exosome-Mimetic Nanovesicles for Targeted Delivery of Chemotherapeutics to Malignant Tumors, ACSNANO, vol. 7, No. 9, p. 7698-7710, 2013.

* cited by examiner

*Primary Examiner* — Michael G. Hartley
*Assistant Examiner* — Jagadishwar R Samala
(74) *Attorney, Agent, or Firm* — The PL Law Group, PLLC

(57) ABSTRACT

A method for labeling exosomes with a radioactive substance using an amine group on surfaces of the exosomes includes providing a cell-derived exosome, treating a surface of the exosome with N-hydroxysuccinimide-azadibenzocyclooctyne (NHS-ADIBO), and mixing the treated exosome with N3-introduced chelator-radioactive substance to conduct a reaction between the chelator and an amine group present on the surface of the exosome, wherein the radioactive substance is introduced inside the exosome by the above reaction. The exosomes can be stably labeled at high labeling efficiency, and the exosomes can be favorably used as an agent for nuclear medicine imaging and therapeutic imaging for confirming the biological distribution of exosomes and whether the exosomes move to target organs and target diseases in animals including a human being.

5 Claims, 9 Drawing Sheets

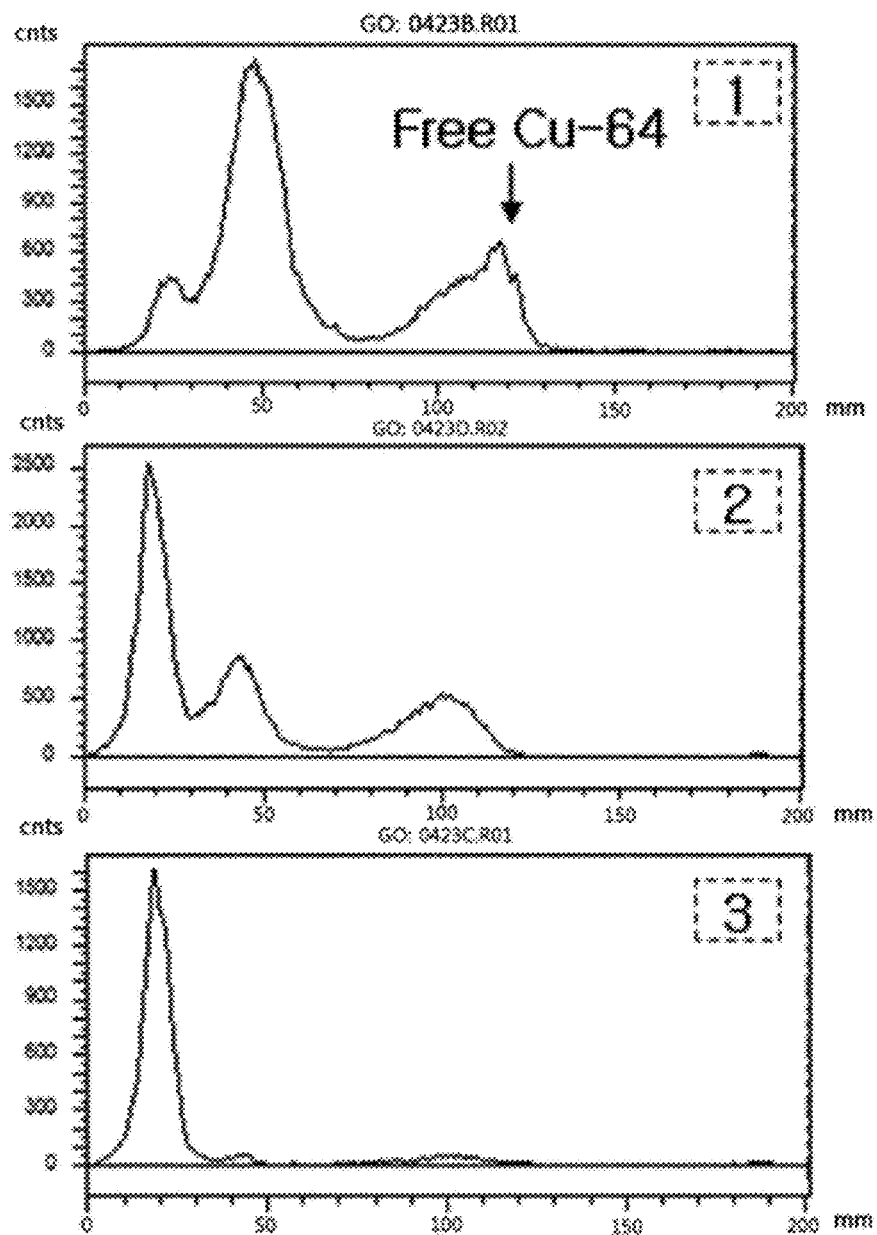

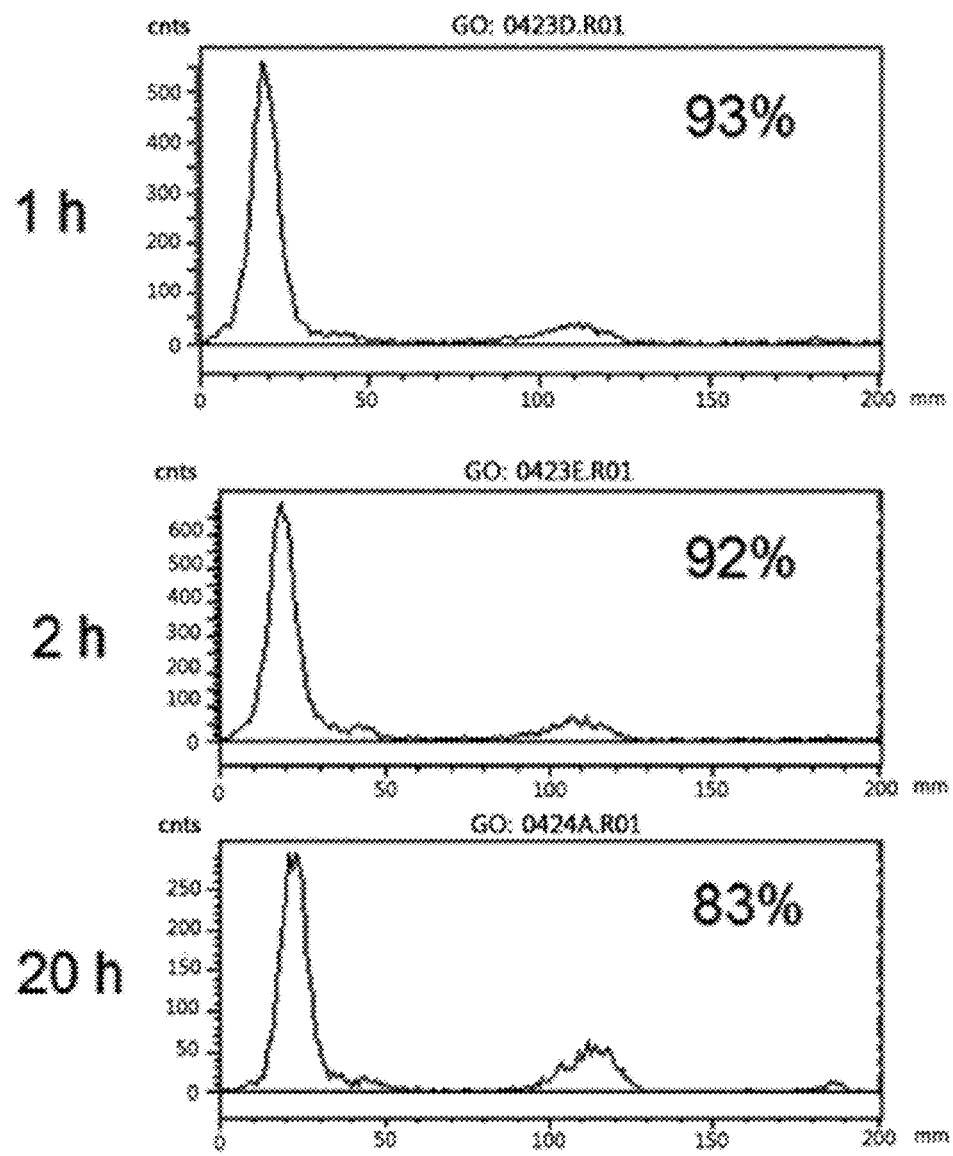

FIG. 3B
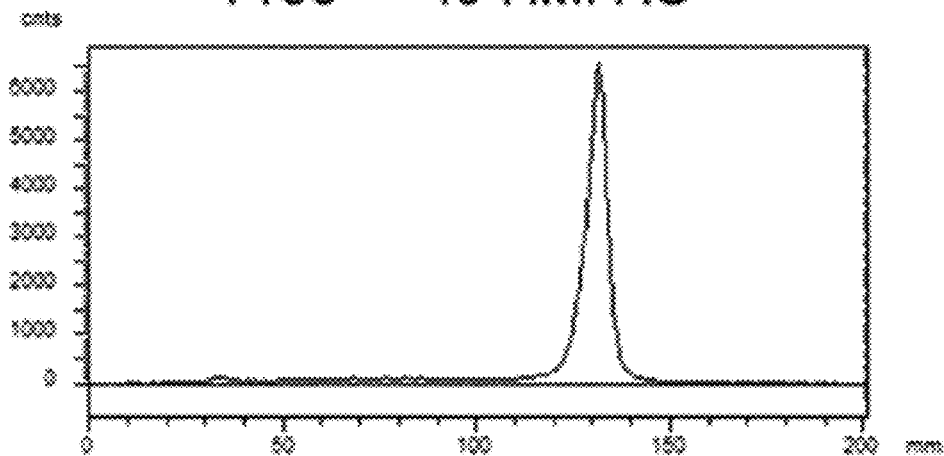
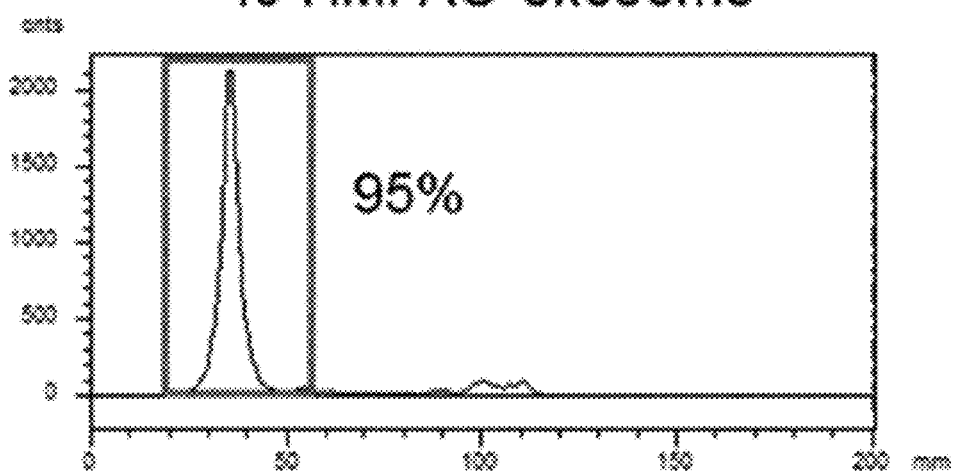

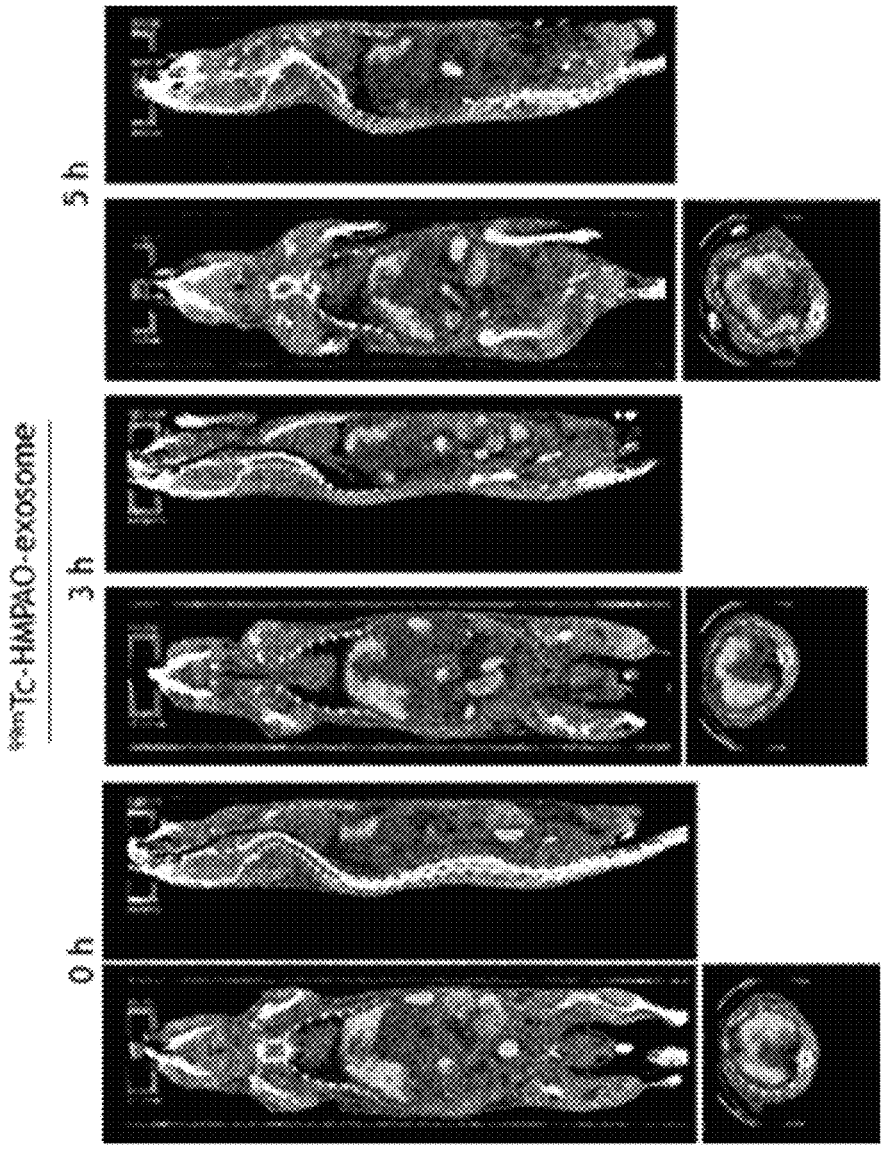

METHOD FOR LABELING EXOSOMES WITH RADIOACTIVE SUBSTANCE AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/004778, filed May 13, 2015, which claims priority to the benefit of Korean Patent Application No. 10-2014-0061609 filed in the Korean Intellectual Property Office on May 22, 2014, the entire contents of which are incorporated herein by reference.

TECHNICAL FIELD

The present invention relates to a technique for labeling exosome with a radioactive substance and use thereof.

BACKGROUND ART

Exosome is a nano-sized vesicle naturally generated in a cell, and contains protein and genetic information to thus deliver diverse signals including the genetic information from the cell to other cells, thereby being involved in development, proliferation, differentiation, immune-modulation, angiogenesis, or progression of different diseases. The exosome as a bio-nanovesicle may avoid immune response and have excellent human-compatibility, and other advantages such as drug loading ability, target delivery effect to specific cells, stability in blood, etc., and therefore, recently drawing a great deal of attention as a drug delivery system.

Conventional liposome-based nanodrug delivery systems are employed in clinical applications. However, some technical limitations such as limited drug delivery efficiency to a target and a problem in releasing desired drug on a lesion site have been exposed. Accordingly, when the exosome is administered to a human body for purpose of playing a role of the drug delivery system, a method for assaying in vivo distribution of the exosome and whether the exosome is reliably delivered to a target organ may be required.

A variety of labeling techniques for image tracer of existing substances of biological origins ('bio-derived') or nano-substances have been proposed. However, in a case of exosome, in aspects of requirement for a labeling technique under physiological and environmental conditions in order to preserve characteristics of the exosome as a bio-derived substance, in addition, procedures and stability for regaining labeled exosome after labeling, it is difficult to label the exosome according to any typical method.

Korean Patent Laid-Open Publication No. 2013-0127276 discloses a method of analyzing exosomes using fluorescent material-labeled exosome, which includes binding the fluorescent material-labeled exosome to a solid support to analyze the exosomes. However, due to high background as a problem of fluorescent image itself, there is a limit to trace fluorescence-based exosome in a living animal.

Accordingly, it is necessary to develop a novel technique that can easily observe in vivo distribution of the exosome and determine whether the exosome moves toward a target organ and/or target disease through a nuclear medical image even in levels of human as well as small animals, due to the exosome is labeled with a material capable of replacing the fluorescent substance.

SUMMARY

An object of the present invention is to provide a method fat labeling exosome that can label the exosome under physiological conditions and obtain stabilized exosome, as well as the exosome labeled with a radioactive substance.

According to an aspect of the present invention, there is provided a method for labeling exosome with radioactive substance, including: providing cell-derived exosome; treating a surface of the exosome with N-hydroxysuccinimide-azadibenzocyclooctyne (NHS-ADIBO); and mixing the treated exosome with N3-introduced chelator-radioactive substance, so as to conduct a reaction of the chelator with an amine group present on the surface of the exosome, wherein the radioactive substance is introduced into the exosome by the above reaction. In the present invention, the exosome refers to an extracellular vesicle, which is a cell-derived material, and includes exosomes and ectosomes possibly secreted out of the cell.

According to one embodiment of the present invention, the N3-introduced chelator used herein is not particularly limited so long as it can react with the NHS-ADIBO through a reaction based on click chemistry, and may include, for example, 1,4,7-triazacyclononane-1,4,7-triacetic acid (NOTA), 1,4,7,10-tetraazacyclododecane-1,4,7,10-tetraacetic acid (DOTA), 3-[6,17-dihyroxy-7,10,18,21-tetraoxo-27-[N-acetylhydroxylamino)-6,11,17,22-tetraazaheptaeicosane]thiourea (DFO), diethylenetriaminepentaacetic acid (DTPA), diaminedithiol (N2S2), 2-(4'-isothiocyanatobenzyl)-1,4,7-triazacyclononane-1,4,7-triacetic acid (p-SCN-Bn-NOTA), 1,4,7-triazacyclononane,1-glutaric acid-4,7-acetic acid (NODAGA), 2-(4'-isothiocyanatobenzyl)-1,4,7,10-tetraazacyclododecane-1,4,7,10-tetraacetic acid (p-SCN-Bn-DOTA), 1,4,8,11-tetraazacyclotetradecane-1,4,8,11-tetraacetic acid (TETA), 2-(4-isothiocyanatobenzyl)-diethylenetriaminepentaacetic acid (p-SCN-Bn-DTPA), 1-(4-isothiocyanatophenyl)-3-[6,17-dihyroxy-7,10,18,21-tetraoxo-27-[N-acetylhydroxylamino)-6,11,17,22-tetraazaheptaeicosane]thiourea (p-SCN-Bn-DFO) or hydrazinonicotinic acid (HYNIC), but it is not limited thereto.

The chelator according to the present invention is labeled with a radioactive isotope, and such a radioactive isotope may include, for example: positron emission nuclides such as $^{18}$F, $^{68}$Ga, $^{64}$Cu, $^{89}$Zr and $^{124}$I; gamma ray emission nuclides such as $^{99m}$Tc, $^{111}$In, $^{123}$I and $^{125}$I; or therapeutic nuclides such as $^{67}$Cu, $^{177}$Lu, $^{90}$Y, $^{186}$Re, $^{188}$Re and $^{131}$I.

The method of the present invention may be executed in a phosphate buffer solution (PBS), for example, at about pH 7.0 to pH 7.4 under physiological conditions.

According to another aspect of the present invention, there is provided the exosome labeled with a radioactive substance, which is prepared by the inventive method.

According to another aspect of the present invention, there is provided an imaging agent including the exosome labeled according to the method of the present invention, wherein the imaging agent may further include a therapeutic material.

According to another aspect of the present invention, there is provided an imaging method, including: administering the imaging agent according to the present invention to in vitro cell or individual; and analyzing a distribution of the administered imaging agent and movement thereof by a radioactive image technique.

The method of the present invention may rapidly and stably label the exosome under physiological environments for preserving characteristics of bio-derived substances, so that in vivo distribution of exosome can be non-invasively gained in animals including a human being by using the exosome prepared according to the inventive method, and whether the exosome moves toward target organs and target diseases can be identified, thereby being effectively applied to nuclear medical images, a therapeutically imaging agent, etc.

BRIEF DESCRIPTION OF THE DRAWING

FIG. 2A illustrates analyzed results of $^{64}$Cu-labeled exosome through thin layer chromatography (TLC). In particular, FIG. 2A illustrates measured values of: 1) a group of $N_3$-PEG4-NOTA labeled with $^{64}$CuCl$_3$; 2) an $N_3$-PEG4-NOTA-$^{64}$Cu+ADIBO-exosome group; and 3) an $N_3$-PEG4-NOTA-$^{64}$Cu+ADIBO-exosome reaction, followed by separation using PD-10.

FIG. 2B illustrates measured results of serum stability of $^{64}$Cu-labeled exosome.

FIG. 3B illustrates analyzed results of $^{99m}$c-labeled exosome through thin layer chromatography (TIC), wherein the exosome remains at the beginning point while free $^{95m}$TcO$_4$— or $^{99m}$Tc-HMPAO moves together with a solvent.

FIG. 4A is photographs of in vivo distribution taken using SPEC/CT at 30 minutes, 3 hours and 5 hours after administration of $^{99m}$Tc-HMPAO-exosome to a mouse.

DETAILED DESCRIPTION

Figure 1:
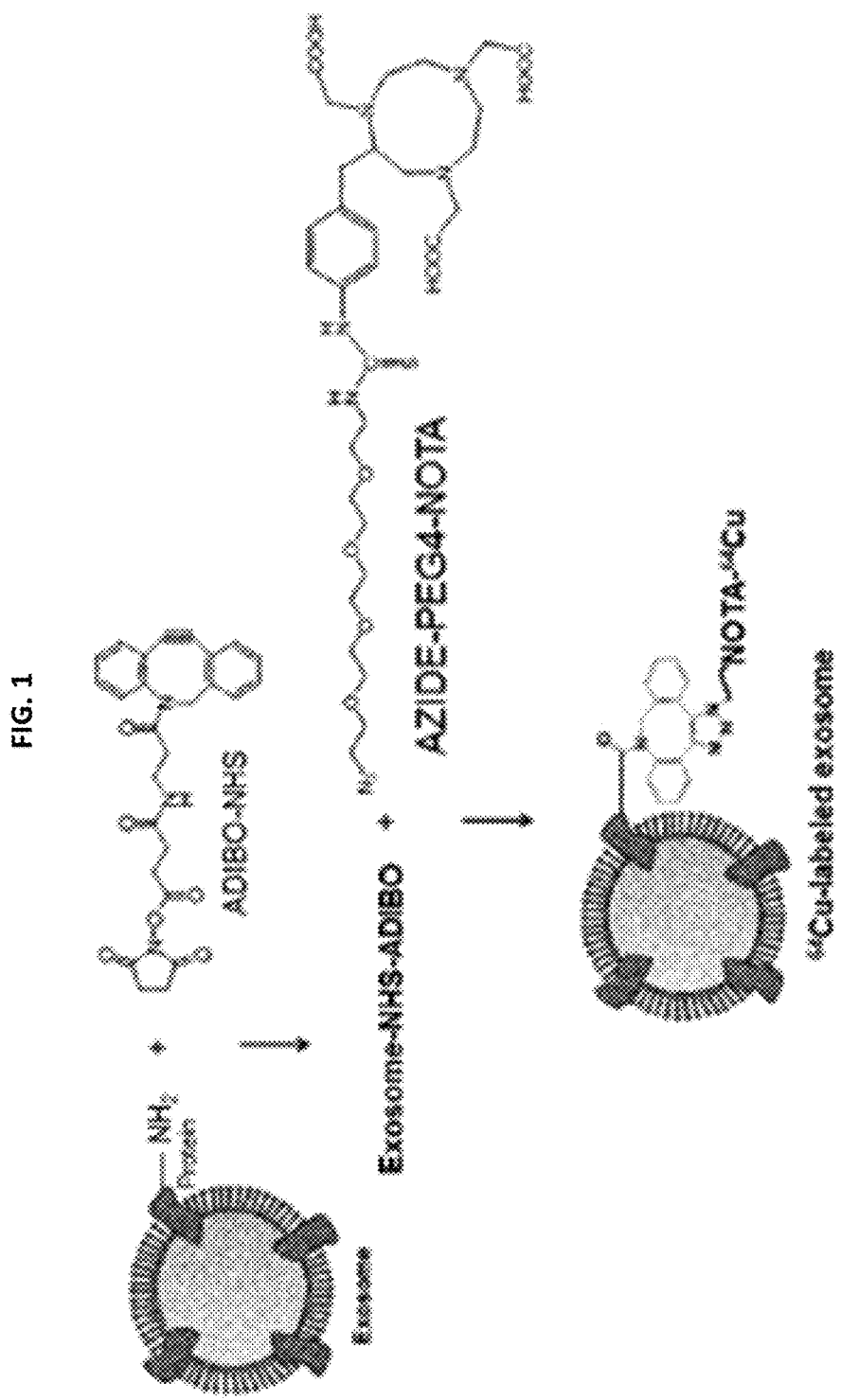
FIG. 1 is a schematic view illustrating a click reaction between N3 azide and ADIBO compound.

The present invention relates to the exosome label, and more particularly, is based on the findings that: a substance capable of freely passing through a double-lipid membrane of the exosome may be captured and used for tracing by conventional techniques such as imaging; and labeling thereof is possibly achieved by introducing an isotope into the exosome through a reaction between a chelator having the isotope bonded thereto and an amine group present on a surface of the exosome.

Accordingly, one aspect of the present invention may provide a method for labeling exosome with a radioactive substance, including: providing cell-derived exosome; treating a surface of the exosome with N-hydroxysuccinimide-azadibenzocyclooctyne (NHS-ADIBO); and reacting the treated exosome with a chelator-radioactive substance able to react with an amine Group present on the surface of the exosome, wherein the radioactive substance is introduced into the exosome by the above reaction.

The exosome refers to a nano-sized vesicle naturally generated in a cell, and contains protein and genetic information to thus deliver diverse signals including the genetic information from the cell to other cells, and therefore, known to be involved in development, proliferation, differentiation, immune-modulation, angiogenesis, progression of different disease, or the like. The exosome may be isolated from diverse cells with reference to conventional techniques known in the related art or the method described in the examples of the present invention.

According to the method of the present invention, the free amine group (NH$_2$) present on the surface of the exosome may react with a chelator linked to a radioactive isotope. Any material may be used as the chelator so long as it can react with the free amine group (NH$_2$), and the chelator may include, without particular limitation thereof, 1,4,7-triazacyclononane-1,4,7-triacetic acid (NOTA), 1,4,7,10-tetraazacyclododecane-1,4,7,10-tetraacetic acid (DOTA), 1,4,8,11-tetraazacyciotetradecane-1,4,8,11-tetraacetic acid (TETA), 3-[6,17-dihydroxy-7,10,18,21-tetraoo-27-[N-acetylhydroxylamino)-6,11,17,22-tetraazaheptaeicosane]thiourea (DFO), diethylenetriaminepentaacetic acid (DTPA), diaminedithiol (N2S2), 2-(4'-isothiocyanatobenzyl)-1,4,7-triazacyclononane-1,4,7-triacetic acid (p-SCN-Bn-NOTA), 1,4,7-triazacyclononane,1-glutaric acid-4,7-acetic acid (NODAGA), 2-(4'-isothiocyanatobenzyl)-1,4,7,10-tetraazacyclododecane-1,4,7,10-tetraacetic acid (p-SCN-Bn-DCTA), 2-(4-isothiocyanatobenzyl)-diethylenetraminepentaacetic acid (p-SCN-Bn-DTPA), 1-(4-isothiocyanatophenyl)-3-[6,17-dihydroxy-7,10,18,21-tetraoxo-27-[N-acetylhydroxylamino)-6,11,17,22-tetraazaheptaeicosane]thiourea (p-SCN-Bn-DLO), or hydrazinonicotinic acid (HYNIC), etc. Further, the radioactive substance labeled on the chelators described above may include radioactive isotopes, for example, positron emission nuclides such as $^{18}$F, $^{68}$Ga, $^{64}$Cu, $^{89}$Zr and $^{124}$I, etc., gamma ray emission nuclides such as $^{99m}$Tc, $^{111}$In, $^{123}$I and $^{125}$I, or therapeutic nuclides such as $^{67}$Cu, $^{177}$Lu, $^{90}$Y, $^{186}$Re, $^{188}$Re and $^{131}$I.

The exosome labeled according to the method of the present invention may prevent a slight amount of material including the radioactive substance from escaping after penetrating the membrane and being metabolized, and may be effectively used for imaging or the like, due to the radioactive substance is placed inside the exosome.

According to the method of the present invention, the reaction between the exosome treated using NHS-ADIBO and the chelator-radioactive substance may be conducted at about pH 7.0 to pH 7.4 and, in particular, in a phosphate buffer solution (PBS) at about pH 7.0 to pH 7.4. The reaction of the chelator having an N3 functional group with the ADIBO compound (click chemistry) may proceed under neutral pH conditions, for example, at room temperature and pH 7.0 to pH 7.4. In this case, the labeling may be effectively achieved without modifying physical properties of the exosome.

The click chemistry means a general method of forming different constitutional parts, and simply and rapidly combining these constitutional parts, so as to produce a specific and desired substance, however, not particularly referring to specific chemical reactions.

Accordingly, another aspect of the present invention provides the exosome prepared by the method of the present invention, and an imaging composition or imaging agent including the same.

The imaging agent of the present invention may be used for imaging a position of cells introduced into the body of animals including the human being with the purpose of analysis or treatment, and therefore, normal or abnormal information in a cellular level, status in progress over time, results of movement and development, etc. may be obtained for a long period of time. In other words, since target imaging of the introduced cells is possible, the imaging agent of the present invention, for example, may be easily used for tracing the expression of cell and a pathway of movement in treatment of cells by administration of stem cells.

A radioactive imaging technique compatible with the imaging agent of the present invention may include positron emission tomography (PET), single photon emission computer tomography (SPECT), gamma ray camera photography, or the like, but it is not particularly limited thereto.

The imaging agent according to the present invention refers to a technique conducting treatment based on image examination, may be used while monitoring drug or gene delivery, and may enable in vivo distribution and targeting a lesion site by using an extremely small amount thereof for labeling with a difficulty in exhibiting toxicity, and thereby being early applicable to clinical applications.

In this regard, the exosome according to the present invention may also be used as a therapeutically imaging agent containing any therapeutic agent therein. Such a therapeutically imaging agent may refer to, for example, an imaginable therapeutic probe, which can endow an imaging function to a pharmaceutical agent for treatment of cancer or the like, in order to treat the cancer while taking images and monitoring, simultaneously. Further, the therapeutically imaging agent may enable 'therapy' and 'diagnosis' at a time, thus referring to 'theragnosis'.

The composition of the present invention may further include a pharmaceutically acceptable carrier. The pharmaceutically acceptable carrier may include, for example, any solvent, dispersible medium, coating agent, isotonic agent, administration enhancer, absorption sustaining agent, or the like, but is not particularly limited thereto. Further, additional active ingredients such as the therapeutic agent described above may also be introduced into the composition. Also, it is possible to adjust the pH and exact concentration thereof depending on the known parameters. Further, some materials required for imaging according to a radioactive imaging technique may be additionally included. The composition of the present invention may be administered through typical routes used in veterinary science and/or medical applications, for example, via intravenous, intraperitoneal, intramuscular, subcutaneous and/or topical routes.

Further, another aspect of the present invention provides an imaging method, including: administering the exosome of the present invention described above, an imaging composition or imaging agent including the same to an individual; and analyzing a distribution and movement of the administered imaging agent by a radioactive imaging technique.

The individual possibly subjected to the method of the present invention may be mammals including the human being. For instance, livestock such as cattle, sheep, goat, cow, pig, etc.; poultry such as chicken, duck, goose, turkey, etc.; pet such as dog, cat, etc.; rodents (for example, mouse, rat, hamster); rabbit, or the like, may be included.

Hereinafter, the following examples would be proposed for more clearly understanding the present invention. However, these examples are provided only for more easily understanding the present invention and it duly appreciated that the present invention would not particularly limited to the examples.

EXAMPLE

Example 1. Preparation of Exosome

Exosome was prepared by a conventional method for producing exosomes at a high yield disclosed in the art (Jang et al., ACS Nano 2013 24; 7:7698-710).

More particularly, a fatal bovine serum (FBS) free from the exosome was prepared by ultra-centrifugation 150,000 g and 4° C. for 16 hours. Raw264.7 cells (mouse-derived macrophages) were cultured at 37° C. for 24 hours using a RPMI medium including 10% exosome-free FBS. Next, the cultured cells were collected and crushed in a phosphate buffer solution (PBS—NaCl 137 mmol/L, KCl 2.7 mmol/L $Na_2NPO_4$ 10 mmol/t, $KH_2PO_4$ 1.8 mmol/L) at 4° C. through ultra-sonication. Following this, the cells including cell residue were removed by continuous centrifugation at 500 g for 10 minutes then at 3000 g for 15 minutes. Lastly, ultra-centrifugation at 150,000 g was executed at 4° C. for 2 hours to result in exosome pellets, followed by re-suspending the exosome pellets in PBS. A final concentration of protein has been set to 1 mg/ml in PBS by quantification through Bradford assays.

Example 2. Labeling of Exosome with $^{64}Cu$ or $^{68}Ga$ or $^{99m}Tc$ (Technetium)

Firstly, ADIBO-NHS was synthesized through a reaction between amine and NHS-ester. For this purpose, the exosome (1 mg/mL) isolated in Example 1 and stored at −80° C. was dispensed in an amount of 200 to 500 μg.

Next, ADIBO-NHS was dissolved in DMSO such that ADIBO-NHS (Futurechem, Korea) reaches 80 μM in 1 mL of the final reaction mixture. That is, after dissolving 3 mg of ADIBO-NHS in 1 ml DMSO, 10 μL of the solution was taken and fed to the mixture, thereby preparing the product including 80 nmole of ADIBO-NHS in 1 mL of the mixture.

All of the reactions have been executed on ice. The prepared exosome solution was adjusted to become 1 mL volume in 1×PBS and 10 μL of ADIBO-NHS dissolved in DMSO was added to the exosome solution, followed by a reaction at 37° C. for 30 minutes. Then, free ADIBO-NHS was separated in a concentration-gradient mode using Opti-prep (Sigma-Aldrich, USA) according to the instruction of the manufacturer. Briefly, in terms of sucrose concentration gradients, 50% Opti-prep and 10% Opti-prep were prepared and placed in a 5 mL test tube. Herein, 0.5 mL of 50% Opti-prep and 1 mL of 10% Opti-prep were fed in this order. Then, the reacted exosome was adjusted to 3 mL using 1×PBS and added to the above solution. Following this, ultra-centrifugation was executed at 100,000 g for 2 hours (100,000 g=32 Krpm). As a result, ADIBO-EXO was obtained between 0.5 mL 50% Opti-prep and 1 mL 10% Opti-prep. After measuring a protein concentration thereof, the above material was stored at −80° C. before using the same.

Then, the obtained ADBIO-EXOSOME was combined with N3-PEG4-NOTA labeled with $^{64}Cu$ or $^{68}Ga$.

First, 10 μL (10 nmole) of N3-PEG-NOTA (1 mg/mL) (Futurechem) was prepared. In order to label the N3-PEG4-NOTA with an isotope, the prepared 10 nmole N3-PEG4-NOTA was mixed with 200 uCi $^{64}CuCl_3$ (or $^{68}GaCl_3$) in 1 M sodium acetate buffer, thereby preparing a total volume of 200 μL. Then, this solution was subjected to a reaction in a stirred flow reactor at pH 5 and 37° C. for 10 minutes. Next, 20 μL of the labeled N3-PEG4-NOTA-$^{64}Cu$ was prepared and adjusted to pH 7 using 2M NaOH, and 50 μL ADIBO-EXOSOME dispersed in 1×PBS was added to the above prepared solution, followed by conducting a reaction. Next, using a size-exclusion column, that is, PD-10 column (GE Healthcare, USA), free $^{54}Cu$ or N3-PEG4-NOTA-$^{64}Cu$ not participating in the reaction was removed. For this purpose, the reaction was conducted in a stirred flow reactor at 37° C. for 20 minutes, and thin layer chromatographic data were obtained by developing instant thin layer chromatography-silica Gel (iTLC-SG) on Whatman no. 1 paper using 0.1 M citric acid, so as to determine label efficiency.

Results of the above experiment are shown in FIG. 2A. As a result of TIC, 50 mm of inherent moving distance of N3-PEG4-NOTA-$^{64}$Cu was determined, and free $^{64}$Cu peaks were identified in a range of 100 to 120 mm. Next, when the $^{64}$Cu-labeled N3-PEG4-NOTA was reacted with ADIBO-exosome, inherent $^{64}$Cu-labeled exosome peaks were observed at a moving distance of 20 mm. However, since N3-PEG4-NOTA-$^{64}$Cu peaks and free $^{64}$Cu peaks were also observed, 99% $^{64}$Cu-labeled exosome was identified when TLC measurement was executed after the reaction of N3-PEG4-NOTA-$^{64}$Cu+ADIBO-exosome and removing N3-PEG4-NOTA-$^{64}$Cu and free $^{64}$Cu with PD-10. Accordingly, it is possible to rapidly and simply label the isotope on the surface of the exosome by the method of the present invention.

In a case of $^{68}$Ga label, the procedures are substantially the same as the above description except that 50 uCi of $^{68}$Ga was used and a total volume was set to be 100 μL.

Figure 3A:
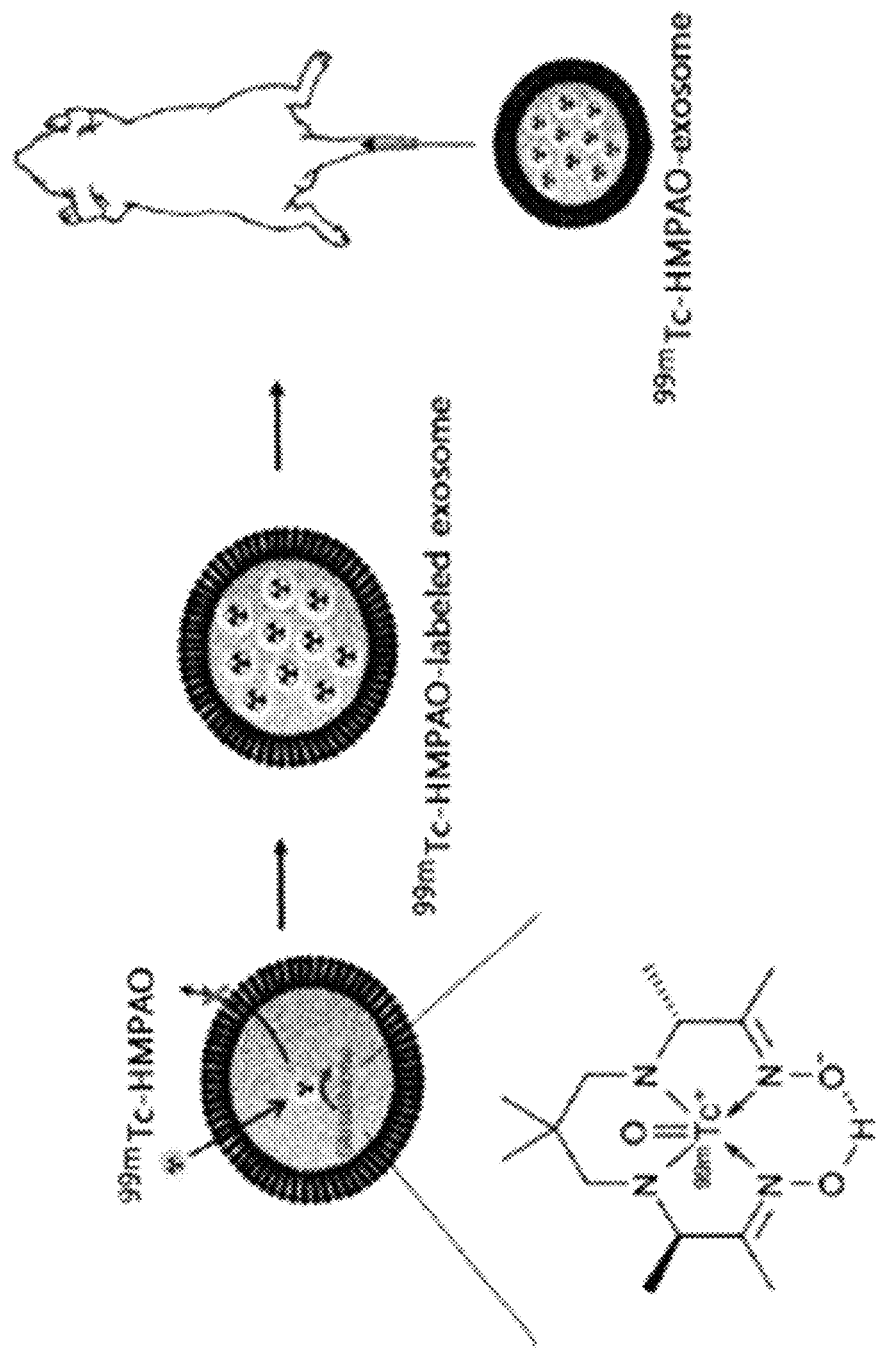
FIG. 3A is a diagram illustrating a labeling method of exosome-mimetic substance nanovesicle (NV) with $^{99m}$Tc-HMPAO.

For $^{99m}$Tc labeling, hexamethylpropyleneamine oxime or HAMPAO kit was used. A reaction relevant to this labeling was illustrated in the diagram of FIG. 3A. The HAMPAO kit (Dong-A Pharmaceutical, Seoul) was labeled with 99mTc without Methylene Blue according the instruction of the manufacturer 50 μg of the exosome prepared in Example 1 as well as 185 MBq of $^{99m}$Tc-HMPAO prepared as described above were cultured at room temperature for 60 minutes. pH value used herein was pH 7.4 of the same as the biological condition. $^{99m}$-HMPAO was introduced into the exosome and irreversibly captured in the exosome due to a reaction with a sulfhydryl group of glutathione. Following this, the exosome was eluted and isolated from the free $^{99m}$TcO$_4$— or $^{99m}$Tc-HMPAO to 0.9% w/v sodium chloride solution using a PD-column (GE Healthcare, USA). The eluted solution was collected in an amount of 0.5 in a test tube. Label efficiency was analyzed by Whatman no. 1 paper and through thin layer chromatography (TLC) using 0.9% NaCl solution as a developing solvent.

The analyzed results are shown in FIG. 3B. As illustrated in this figure, it was found that the exosome has remained at the beginning point on TLC, while the free $^{99m}$TcO$_4$— or $^{99m}$Tc-HMPAO moved together with the solvent. A radioactive chemical purity was determined as 93.78%. The measured serum label stability of the corresponding label exosome was 92.8% at 10 minutes, 90.6% at 30 minutes and 71.2% at 1 hour.

Further, as a study precedent for in vivo application of the exosome labeled with $^{64}$Cu, serum stability was determined. After isolating the serum from blood of a human being, the $^{64}$Cu-labeled exosome prepared in the above example was reacted with the corresponding serum at room temperature (a temperature of 25° C. in a laboratory) for 1 hour, 2 hours and 20 hours, respectively. Results of the reaction were analyzed through thin layer chromatography (TLC).

The analyzed results are shown in FIG. 2B. As shown in this figure, when the reaction was carried in the serum for 1 hour, 93% stability was identified. After 2 hours, high stability of 92% was observed. Further, even after 20 hours, the serum stability was 83% to thus exhibit the result of high stability. These results demonstrated that the method for labeling exosome according to the present invention has excellent stability.

Example 3. SPECT/CT Using $^{99m}$Tc Labeled Exosome 0.2 to 0.4 mCi of $^{99m}$Tc-HMPAO-exosome prepared in Example 2 was administered to tail veins of total three mice (Balb/c type, Orient-bio, 20-25 g, 10-15 weeks old) through intravenous injection. SPECT/CT photographing was executed using a SPECT/CT scanner (NanoSPECT/CT, Bioscan, Washington, D.C.) on 30 minutes, 3 hours and 5 hours after the administration. All of the mice were anesthetized and such anesthetized condition was maintained with 1.5% isoflurane under 1 L/min of oxygen supply. Further the mice were kept in prone position on the scanner. In order to enable high contrast collimation, four (4) multi-pinholes γ-detectors (9-pinholes) were used. Further, in order to identify anatomical position, CT scanning was additionally executed after SPECT. An image acquisition time was controlled so as to exceed 30,000 counts per projection. For SPECT image, 24 projections were obtained with 512×512 acquisition matrices. After then, the images were reconstructed according to OSEM (3-Dimensional Ordered-Subsets Expectation Maximum) algorithm. Radiation in each of organs was compared to a relative count presumed in the SPECT image to calculate a volume of interest (VOI). The count was normalized by IID/g.

Further, the mice were sacrificed at 0, 1, 3 and 5 hours after the administration of $^{99m}$Tc-HMPAO-exosome, and subjected to measurement of radioactivity, thereby conducting quantification of in vivo distribution.

Figure 4B:
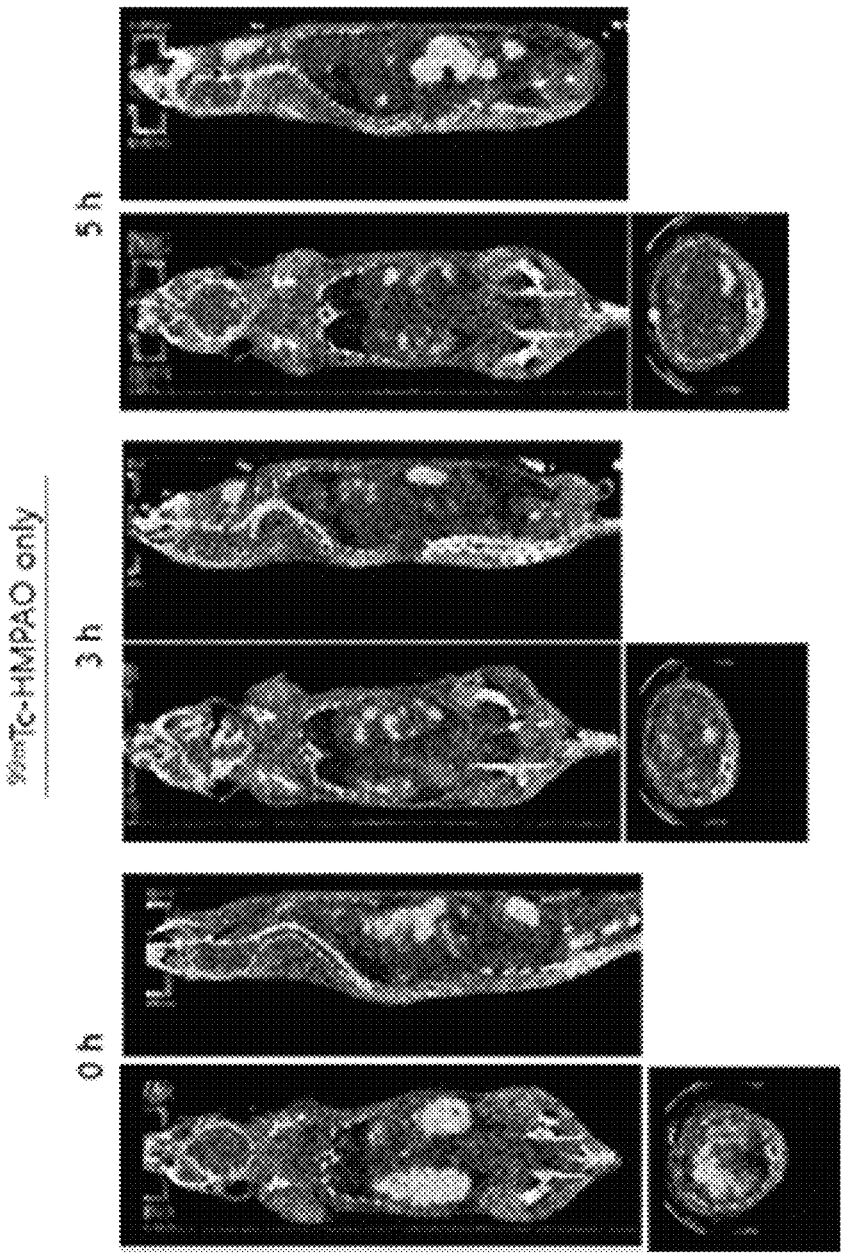
FIG. 4B is photographs of in vivo distribution taken when administering $^{99m}$Tc-HMPAO to a mouse as a control group.
Figure 4C:
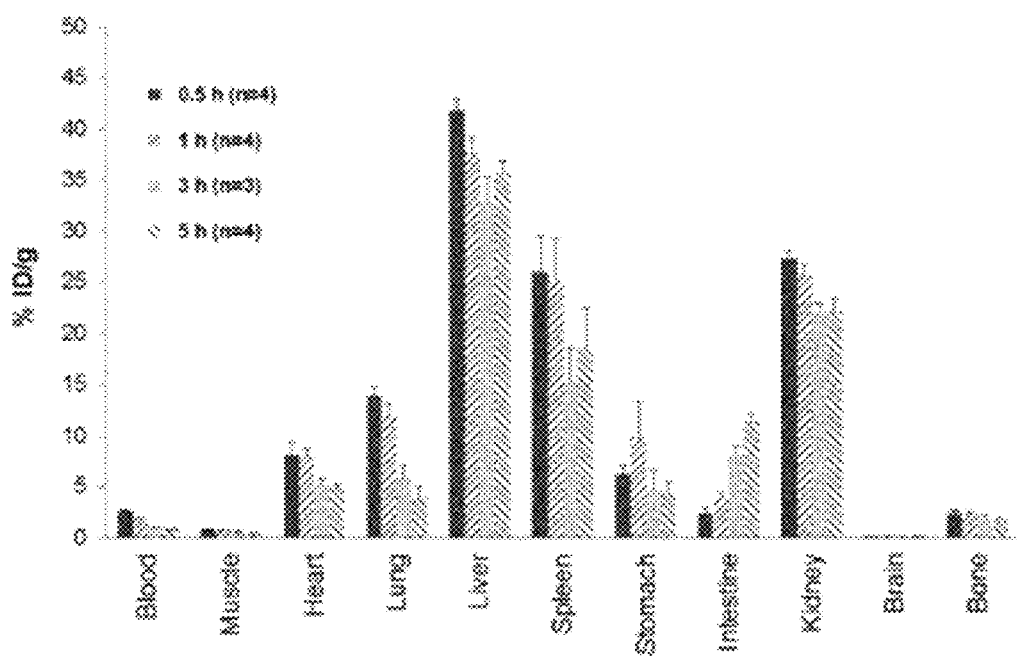
FIG. 4C is graphs illustrating in vivo distribution when administering $^{99m}$Tc-EMRAO-exosome to a mouse.

Results of the measurement are shown in FIGS. 4A, 4B and 4C. As shown in these figures, it was found that the labeled exosome was accumulated in the liver, spleen and kidneys while not being detected in a significant level in the brain, compared to the control group.

Such results as described above would demonstrate that in vivo distribution images may be repeatedly collected over time in non-invasive mode according to the labeling method of exosome according to the present invention, and this means that: whether the exosome is delivered to target organs, in particular, specific target organs, could be directly assessed through images, so as to use the exosome as a drug.

Figure 5:
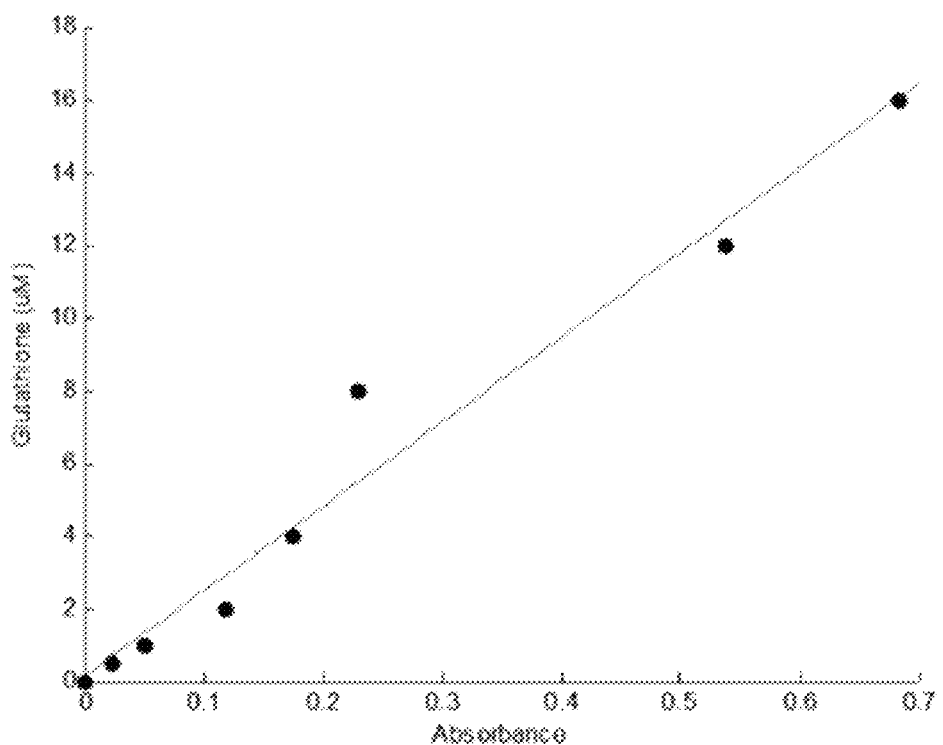
FIG. 5 illustrates results of glutathione analysis conducted using the exosome prepared according to one embodiment of the present invention, showing that 3.15±0.16 nmol of glutathione was detected when using 0.1 mg exosome sample; a red line exhibited a standard curve drawn using known glutathione concentration; and results thereof are shown in mean±SD.

Further, in order to determine whether the exosome can carry endogenous glutathione, the exosome produced in mouse Raw 264.7 macrophage cell-line described above was purified using OptiPrep density-gradient fractions (Sigma-Aldrich, USA) according to the instruction of the manufacturer. Results thereof are shown in FIG. 5.

Glutathione in the exosome was measured by determining whether $^{99m}$Tc-HMPAO label is present, and it was detected that 3.15±0.16 nmol of glutathione is present in 0.1 mg of the exosome.

Hereinabove, illustrative examples of the present invention have been described in detail. However, the scope of the present invention is not limited to these examples. Instead, a variety of modifications and improvements prepared by those skilled in the art on the basis of the principal concept of the present invention defined in the appended claims are duly included in the scope of the present invention.

All technical and scientific terminologies used herein may be used with the same meanings as generally understood by persons having common knowledge in the field to which the present invention pertains, otherwise defined. Entire contents of the published documents introduced as references in the present specification may be incorporated into the present invention.

The invention claimed is:
1. A method for labeling exosome with a radioactive substance, the method comprising:
providing a cell-derived exosome;
treating a surface of the exosome with N-hydroxysuccinimide-azadibenzocyclooctyne (NHS-ADIBO); and mixing the treated exosome with N3-introduced chelator-radioactive substance to conduct a reaction between the chelator and an amine group present on the surface of the exosome, wherein the radioactive substance is introduced inside the exosome by the above reaction.

2. The method according to claim 1, wherein the N3-introduced chelator is selected from 1,4,7-triazacyclononane-1,4,7-triacetic acid (NOTA), 1,4,7,10-tetraazacyclododecane-1,4,7,10-tetraacetic acid (DOTA), 3-[6,17-dihyroxy-7,10,18,21-tetraoxo-27-[N-acetylhydroxylamino)-6,11,17,22-tetraazaheptaeicosane]thiourea (DFO), diethylenetriaminepentaacetic acid (DTPA), diaminedithiol (N2S2), 2-(4'-isothiocyanatobenzyl)-1,4,7-triazacyclononane-1,4,7-triacetic acid (p-SCN-Bn-NOTA), 1,4,7-triazacyclononane,1-glutaric acid-4,7-acetic acid (NODAGA), 2-(4'-isothiocyanatobenzyl)-1,4,7,10-tetraazacyclododecane-1,4,7,10-tetraacetic acid (p-SCN-Bn-DOTA), 1,4,8,11-tetraazacyclotetradecane-1,4,8,11-tetraacetic acid (TETA), 2-(4-isothiocyanatobenzyl)-diethylenetriaminepentaacetic acid (p-SCN-Bn-DTPA), 1-(4-isothiocyanatophenyl)-3-[6,17-dihyroxy-7,10,18,21-tetraoxo-274N-acetylhydroxylamino)-6,11,17,22-tetraazaheptaeicosane]thiourea (p-SCN-Bn-DFO) or hydrazinonicotinic acid (HYNIC).

3. The method according to claim 1, wherein a radioactive isotope linked to the chelator is any one of positron emission nuclides including $^{18}$F, $^{68}$Ga, $^{64}$Cu, $^{89}$Zr and $^{124}$I, gamma ray emission nuclides including $^{99m}$Tc, $^{111}$In, $^{123}$I and $^{125}$I, or therapeutic nuclides including $^{67}$Cu, $^{177}$Lu, $^{90}$Y, $^{186}$Re, $^{188}$Re and $^{131}$I.

4. The method according to claim 1, wherein the reaction between the treated exosome and the chelator-radioactive substance is conducted at pH 7.0 to pH 7.4.

5. The method according to claim 4, wherein the reaction between the treated exosome and the chelator-radioactive substance is conducted in a phosphate buffer solution.

* * * * *